United States Patent [19]

Zimmerschied et al.

[11] 4,014,945

[45] Mar. 29, 1977

[54] PROCESS FOR THE PREPARATION OF ETHYLENE GLYCOL

[75] Inventors: Wilford J. Zimmerschied; David A. Palmer, both of Naperville, Ill.; Ralph J. Bertolacini, Chesterton, Ind.

[73] Assignee: Standard Oil Company, Chicago, Ill.

[22] Filed: Aug. 28, 1975

[21] Appl. No.: 608,553

[52] U.S. Cl. .................. 260/635 E; 260/340.6; 260/601 R; 260/615 R
[51] Int. Cl.$^2$ .................................. C07C 29/00
[58] Field of Search ............. 260/635 E; 252/437

[56] References Cited
UNITED STATES PATENTS

| | | | |
|---|---|---|---|
| 2,770,656 | 11/1956 | Pye | 260/635 E |
| 3,028,434 | 4/1962 | Weisz | 260/635 E |
| 3,475,499 | 10/1969 | Winnick | 260/635 E |
| 3,904,550 | 9/1975 | Pine | 252/437 |

*Primary Examiner*—Joseph E. Evans
*Attorney, Agent, or Firm*—Robert E. Sloat; Arthur G. Gilkes; William T. McClain

[57] ABSTRACT

The present disclosure relates to the catalytic hydration of alkylene oxides, in particular ethylene oxide for the production of glycols using a catalyst comprising a copper promoted aluminum phosphate. In certain instances the isomerization activity of the catalyst can be reduced by the incorporation of small quantities of alkali or alkaline earth metals as inhibitors for such process.

12 Claims, No Drawings

PROCESS FOR THE PREPARATION OF ETHYLENE GLYCOL

BACKGROUND OF THE INVENTION

1. Field of the Art

The field of art to which this invention pertains is catalytic preparation of alkylene glycols and in particular the production of ethylene glycol through the hydration over a specific catalyst of ethylene oxide.

2. Description of the Prior Art

Relevant prior art concerning the present invention can be found in Classes 260-635 or Class 252-437.

In particular, U.S. Pat. No. 2,770,656, issued Nov. 13, 1956, relates to the general preparation of ethylene glycol utilizing a catalyst comprising a specifically defined material. The patent is directed to the vapor phase hydration of ethylene oxide for the production of ethylene glycol by passing a mixture of water and ethylene oxide over a catalyst which comprises a normal calcium orthophosphate at specified reaction temperatures.

It is noteworthy that in this reference there is a failure to describe the use of specified catalysts as claimed by the applicants herein.

SUMMARY OF THE INVENTION

The present invention can generally be summarized as a process for the production of alkylene glycols by the reaction of an alkylene oxide and water over a catalyst comprising aluminum phosphate containing a copper promoter. In a most specific instance the invention can be summarized as a process for the production of ethylene glycol from the reaction of water and ethylene oxide over a copper promoted aluminum phosphate catalyst.

In a broad embodiment the present invention relates to a process for production of ethylene glycol which comprises contacting at reaction conditions a mixture of ethylene oxide and water with a catalyst comprising aluminum orthophosphate to effect the production of ethylene glycol.

DETAILED DESCRIPTION OF THE INVENTION

The specific need for catalytic processes for the production of ethylene glycol are well known. Utility for ethylene glycol includes its use as engine coolants and in the production of polyester fibers or fabrics when the ethylene glycol is combined with dimethylphthalates.

In the production of ethylene glycol, theoretically one mole of water is required to hydrate one mole of ethylene oxide. Actually, however, greater than equal molecular proportions of water to ethylene oxide are required for good results. Although a conversion of approximately 90% can sometimes be obtained when employing a reactant ratio of water to ethylene oxide of around 2, reactant ratios of greater than 6 are generally required to achieve reasonably high yields of products, otherwise the ethylene glycol formed reacts with ethylene oxide to form di- and triethylene glycols. The effects of the reactant ratios on the results obtained for the production of ethylene glycol and other alkylene glycols are well known. Accordingly, in reacting ethylene oxide with water it is preferred that the reaction take place in a vapor phase wherein steam and ethylene oxide are passed over the specified catalyst in a suitable mole ratio for production of ethylene glycol. In reacting steam and ethylene oxide in a ratio of at least 17:1 over a stationary bed of the claimed catalyst, yields based on the ethylene oxide consumed are found to be reasonably high.

Reaction temperatures generally can vary anywhere from about 400° to about 750° F. with a preferred range somewhere below 500°-600° F. Inasmuch as it has been determined that the catalyst of this invention will deteriorate quite rapidly at processing temperatures approaching 550°-650° F it is preferred that the processing conditions be maintained below those temperatures in order to at least maintain some activity of the catalyst for the production of ethylene glycol. In fact, the preferred temperatures range anywhere from around 400°-550° F.

Operating pressures are chosen to obtain the desired yield and production level of ethylene glycol. Generally the pressures can range anywhere from around atmospheric to 1,000 p.s.i.g. or higher. Preferably, the pressure should vary from about 50 to about 300 psig in order to allow adequate production of ethylene glycol with a minimum of side reaction products.

The contacting time of the reactants over a catalyst can vary anywhere from period of less than a second to periods ranging up to 25 seconds. It is anticipated that low contact times be used in order to reduce the tendency for isomerization of ethylene glycol to other moieties and to reduce undesirable side reactions which normally would occur at longer contact times of reactants over the catalyst. The specific physical method of contacting the feed materials over the catalyst can include many process configurations. Accordingly, both fluidized and fixed bed reaction zones can be utilized to effect production of ethylene glycol according to this invention. It is generally assumed that when employing a stationary bed of catalyst it is generally necessary to use somewhat higher ratios of water to ethylene oxide as compared to a fluidized bed contacting over a similar or identical catalyst.

The catalyst which is utilized in the process of the claimed invention is described as an aluminum phosphate catalyst ($AlPO_4$) which contains from about 0.05 to about 10% by weight of copper as a promoter. In a preferred instance the copper is present in a range of from about 0.1 to about 3% by weight and in a most preferred instance the percentage of copper varies from about 0.1 to about 1.5% of the aluminum phosphate catalyst. The particular function of the copper is not necessarily known but it is thought that its use will help in increasing the activity of the catalyst and also to reduce side reaction products.

The catalyst preferably should contain minor portions of alkali or alkaline earth metals or mixtures thereof so as to reduce the isomerization tendency of this catalyst. In this regard, it is especially preferred that the alkali or alkaline earth metal or mixtures thereof be present anywhere from about 0.1 to about 1.5 weight percent of the total catalyst (to include both copper and aluminum phosphate).

The catalyst used is thought to contain aluminum phosphate in the chemical formula of $AlPO_4$. In certain instances, especially when the catalyst is produced from the reaction of an unhydrated aluminum nitrate and phosphoric acid, the catalyst should be calcined at temperatures below 900° F.

Experimental evidence indicated that an aluminum phosphate catalyst with about 1 percent by weight copper which was calcined at 900° F. had essentially no activity for the production of ethylene glycol. The reason for such occurrence can be attributed to the many factors, one of which is theorized as a substantial reduction in the surface area of the catalyst when calcined at these higher temperatures. An alternate theory is that at temperatures above about 550°–600° F. the catalyst originally present as aluminum phosphate ($AlPO_4$) is converted to a different form of phosphate which may have little activity for the hydration of alkylene oxides to alkylene glycols.

Therefore keeping calcination temperatures for catalyst production below 900° F. is necessary. Preferably the catalyst should not be exposed to temperatures above about 600° F. during production and during processing use.

The catalyst performance allows hydration of ethylene oxide at process conditions which permit essentially direct passage of the ethylene oxide reactor effluent to the claimed process. This has a substantial advantage in that a minimum of process treatment is required between the ethylene oxide reaction zone and the present process.

The following examples are presented to generally describe methods of production of the catalyst and process use thereof for the production of ethylene glycol from steam and ethylene oxide. Of course, the present examples are not presented so as to not unduly limit the scope and intended coverage of the appended claims.

In the following examples percent conversion is defined as the moles of ethylene oxide consumed over the moles of ethylene oxide charged times 100. Selectivity based on ethylene oxide consumed is defined as the percent of ethylene oxide converted to the stated products.

EXAMPLE 1

In this example a catalyst was prepared according to the specific requirements for process use of this invention. $Al(NO_3)_3 \cdot 9H_2O$ (465 grams) was dissolved in 200 milliliters of water. To such mixture was added 53 milliliters of an 85% phosphoric acid which had been diluted with 150 milliliters of distilled water. The mixture was cooled to 0° C. with dry ice and 500 milliliters of ethylene oxide was added slowly with stirring so that the temperature did not exceed 10° C. The mixture was allowed to warm to room temperature overnight. The resulting clear gel was dried at about 250° F. for 18 hours. A yield of the dried product was found to be approximately 213 grams.

50 grams of the dried gel were impregnated with 1.9 grams of $Cu(NO_3)_2 \cdot 3H_2O$ dissolved in 50 milliliters of acetone. After impregnation the total sample was dried and then heated to 300° F. for 3 hours.

The resulting catalyst was used in Examples 2, 3, and 4 below.

EXAMPLE 2

Five grams of the catalyst described in Example 1 were mixed with 14.3 grams of ground glass and charged to a ¾ inch by 18 inch electrically heated tube furnace. A feed mixture consisting of approximately 10.9 mol percent ethylene oxide, 74.5 mole percent water as steam and 14.8 mole percent nitrogen was passed over the catalyst at a gas flow rate of 7,180 milliliters per hour per gram of catalyst in the reaction zone. The pressure was essentially atmospheric and the maximum temperature in the reaction zone was 482° F. Analysis of the product of gas chromatographic means showed that ethylene oxide conversion was approximately 77.9%. Based on the ethylene oxide that reacted the selectivities were as follows in the table below.

TABLE 1

| Compound | Selectivity, mol % |
| --- | --- |
| Ethylene glycol | 34.6 |
| Acetaldehyde | 17.9 |
| Ethanol | 4.9 |
| Dioxane | 25.5 |
| Diethylene glycol | 17.1 |

EXAMPLE 3

Ten grams of the copper promoted aluminum phosphate catalyst described in Example 1 were mixed with an equal volume of ground glass and charged to the reactor described in Example 1. The feed composition contained approximately 80 mol% water, 6.06 mol% ethylene oxide and 13.8 mol% of nitrogen. The feed charge rate was approximately 2,950 milliliters per hour per gram of catalyst. A maximum temperature in the catalyst bed of 510° F. was maintained and the operating pressure was approximately 50 p.s.i.g. Conversion of ethylene oxide and approximately 90.4%. Product selectivity based on ethylene oxide converted was as follows:

TABLE 2

| Compound | Selectivity, mol. % |
| --- | --- |
| Ethylene glycol | 57.4 |
| Acetaldehyde | 4.0 |
| Ethanol | 0.2 |
| Dioxane | 9.6 |
| Diethylene glycol | 28.8 |

EXAMPLE 4

The same catalyst as was used in Examples 1 and 2 was used in this experiment. The operating conditions including feed composition were also maintained as described in Example 3 above except that the pressure was 100 psig. Conversion of the ethylene oxide was approximately 94.7%. The selectivities of the product based on ethylene oxide conversion or loss are shown in the table below.

TABLE 3

| Compound | Selectivity, mol% |
| --- | --- |
| Ethylene glycol | 50.6 |
| Acetaldehyde | 1.6 |
| Ethanol | 0 |
| Dioxane | 1.5 |
| Diethylene glycol | 46.2 |

EXAMPLE 5

In this example a catalyst was prepared as described in Example 1 except that after impregnation with copper the catalyst was calcined at 900° F for 3 hours.

The catalyst was found to have essentially no activity for hydration of ethylene oxide to ethylene glycol confirming the requirement for low temperature calcination.

We claim as our invention:

1. A process for production of ethylene glycol which comprises contacting at reaction conditions a mixture of ethylene oxide and water with a catalyst essentially consisting of aluminum phosphate and containing from about 0.05 to about 10 percent by weight of copper based on aluminum phosphate which catalyst has been calcined at a temperature of less than 900° F. to effect the production of said glycol.

2. The process of claim 1 further characterized in that said catalyst contains from about 0.1 to about 3 percent by weight of copper.

3. The process of claim 1 further characterized in that said reaction conditions include a temperature within the range of from about 300° to about 600° F.

4. Claim 3 in that said temperature is within the range of from about 400° to about 550° F.

5. The process of claim 1 further characterized in that said reaction conditions include a pressure within the range of from about 50 to about 300 p.s.i.g.

6. The process of claim 1 further characterized in that said reaction conditions include a molar ratio of water to ethylene oxide of from about 2 to about 50.

7. Claim 6 in that said molar ratio is from about 6 to about 20.

8. The process of claim 1 further characterized in that said catalyst contains less than about 1 percent by weight of a metal selected from the group consisting of alkaline earth metal, alkali metal or mixtures thereof.

9. The process of claim 1 further characterized in that said catalyst is produced by a process in which it is calcined at a temperature of less than about 600° F.

10. A process for the production of ethylene glycol which comprises contacting at reaction conditions including a molar ratio of water to ethylene oxide of from about 6 to about 20, a temperature of from about 400° to about 550° F. and a pressure of from about 50 to about 300 psig, a mixture of water and ethylene oxide with a catalyst essentially consisting of an aluminum phosphate catalyst containing from about 0.1 to about 3 percent by weight of copper which catalyst has been calcined at a temperature of less than 900° F. to effect the production of ethylene glycol.

11. A process for production of ethylene glycol which comprises contacting, at reaction conditions including a molar ratio of water to ethylene oxide of from about 6 to about 20, a temperature of from about 400° to about 550° F. and a pressure of from about 50 to about 300 psig, a mixture of water and ethylene oxide with a catalyst consisting essentially of an aluminum phosphate containing from about 0.1 to about 3 percent by weight of copper which catalyst has been contacted by being calcined at less than 900° F. to effect the production of ethylene glycol.

12. The process of claim 11 further characterized in that said catalyst contains less than about 1 percent by weight of a metal selected from the group consisting of alkaline earth metal, alkaline metal, or mixtures or oxides thereof.

* * * * *